US008413515B2

(12) United States Patent
Isobe et al.

(10) Patent No.: US 8,413,515 B2
(45) Date of Patent: Apr. 9, 2013

(54) ULTRASONIC INSPECTION APPARATUS

(75) Inventors: Hideo Isobe, Tokyo (JP); Hirokazu Karasawa, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/918,904

(22) PCT Filed: Feb. 26, 2009

(86) PCT No.: PCT/JP2009/053600
§ 371 (c)(1),
(2), (4) Date: Aug. 23, 2010

(87) PCT Pub. No.: WO2009/107745
PCT Pub. Date: Sep. 3, 2009

(65) Prior Publication Data
US 2011/0000299 A1  Jan. 6, 2011

(30) Foreign Application Priority Data

Feb. 26, 2008 (JP) ................................. 2008-044307

(51) Int. Cl.
*G01N 29/265* (2006.01)
(52) U.S. Cl. ........................................... 73/634; 73/602
(58) Field of Classification Search .................... 73/602, 73/633, 634, 640
See application file for complete search history.

(56) References Cited

U.S. PATENT DOCUMENTS

| 3,678,736 A * | 7/1972 | May .................................. 73/634 |
| 3,898,838 A * | 8/1975 | Connelly ........................ 73/634 |
| 3,978,714 A * | 9/1976 | Shraiber et al. ................. 73/625 |
| 4,881,177 A | 11/1989 | McClean et al. |
| 5,214,616 A * | 5/1993 | Terhune et al. ................. 367/99 |
| 5,335,547 A | 8/1994 | Nakajima et al. |
| 6,378,376 B1* | 4/2002 | Derman et al. ................. 73/606 |
| 7,181,970 B2 | 2/2007 | Haase et al. |
| 7,448,271 B2 | 11/2008 | Duncan et al. |
| 7,496,456 B2* | 2/2009 | Hiyama et al. .................. 702/39 |

(Continued)

FOREIGN PATENT DOCUMENTS

| JP | 58-166195 U | 11/1983 |
| JP | 63-309852 A | 12/1988 |

(Continued)

OTHER PUBLICATIONS

U.S. Appl. No. 12/918,907, filed Aug. 23, 2010, Isobe.

(Continued)

*Primary Examiner* — Peter Macchiarolo
*Assistant Examiner* — Rose M Miller
(74) *Attorney, Agent, or Firm* — Foley & Lardner LLP

(57) ABSTRACT

There is provided an ultrasonic inspection apparatus which detects various deviations with respect to an ideal scanning position and achieves, with high accuracy, an ultrasound flaw inspection by autonomously adjusting the deviations. The ultrasonic inspection apparatus according to the present invention is provided with an integrated type ultrasound transducer including an ultrasonic transducer, an integral type ultrasound transducer control unit, an actuator for distance adjustment, an actuator for tilt control, and a distance measuring sensor. The integrated type ultrasound transducer calculates a deviation between a scanning position based on a preliminarily generated scanning path information and an ideal scanning position, and performs a deviation correction processing by autonomously controlling a distance and a tilt between an opening surface of the ultrasound transducer and an inspection region of an object to be inspected in accordance with this deviation.

6 Claims, 10 Drawing Sheets

U.S. PATENT DOCUMENTS

| | | | |
|---|---|---|---|
| 7,891,248 B2* | 2/2011 | Hough et al. | 73/634 |
| 7,921,575 B2* | 4/2011 | Little et al. | 33/503 |
| 8,100,015 B2* | 1/2012 | Karasawa et al. | 73/602 |
| 8,179,132 B2 | 5/2012 | Wu et al. | |
| 2007/0039390 A1 | 2/2007 | Duncan et al. | |
| 2009/0288490 A1 | 11/2009 | Maruyama et al. | |

FOREIGN PATENT DOCUMENTS

| | | | |
|---|---|---|---|
| JP | 03-077057 A | 4/1991 | |
| JP | 05-045347 A | 2/1993 | |
| JP | 2553867 B2 | 8/1996 | |
| JP | 2720077 B2 | 11/1997 | |
| JP | 2005-106654 A | 4/2005 | |
| JP | 2005-300363 A | 10/2005 | |
| JP | 3766210 B2 | 2/2006 | |
| JP | 2006-317417 A | 11/2006 | |
| JP | 2007-192649 A | 8/2007 | |
| WO | WO 2007/021541 A2 | 2/2007 | |

OTHER PUBLICATIONS

Translation of International Preliminary Report on Patentability of PCT/JP2009/053600, dated Oct. 5, 2010, 7 pages.

Translation of International Preliminary Report on Patentability of PCT/JP2009/053601, dated Oct. 5, 2010, 6 pages.

H. Isobe, U.S. PTO Notice of Allowance, U.S. Appl. No. 12/918,907, dated Oct. 1, 2012, 9 pages.

H. Isobe, U.S. PTO Office Action, U.S. Appl. No. 12/918,907, dated Jun. 21, 2012, 10 pages.

* cited by examiner

ULTRASONIC INSPECTION APPARATUS

TECHNICAL FIELD

The present invention relates to an ultrasonic inspection apparatus, and more particularly to an ultrasonic inspection apparatus that performs scanning with high accuracy in an ultrasonic flaw inspection.

BACKGROUND ART

To inspect a defect in a structure or a component, or a peeling state of a void or a joint, an ultrasonic inspection apparatus is used that can visualize such a state. The ultrasonic inspection apparatus uses an ultrasonic transducer constituted by a piezoelectric conversion unit formed into a matrix or linear array shape to scan an object to be inspected and inspect a defect or the like.

The ultrasonic inspection apparatus includes a scanner mechanism that drives the ultrasonic transducer. The scanner mechanism is constituted by a Cartesian robot having an X-axis, a Y-axis, a Z-axis, and a required axis such as an A-axis (rotation axis in an X-axis direction), a B-axis (rotation axis in a Y-axis direction), or a C-axis (rotation axis in a Z-axis direction), or an industrial robot basically including an arm mechanism. The scanner mechanism is driven based on control by a control mechanism or the like, and thus the ultrasonic transducer mounted to the scanner mechanism automatically performs a flaw inspection of a predetermined range on a surface of the object to be inspected.

For the ultrasonic transducer to automatically perform a flaw inspection of a predetermined range, scanning path information of the scanner mechanism needs to be previously generated. The scanning path information is generated based on a surface shape of the object to be inspected, for example, with an opening width of the ultrasonic transducer as one scanning width.

A method of generating scanning path information includes a method of previously generating scanning path information using computer software based on shape design data of an object to be inspected. By this method, scanning path information can be relatively easily prepared. However, the prepared scanning path information is scanning path information based on ideal shape design data, and there is a possibility that a shape of an actual object to be inspected does not match a shape of the object to be inspected on the shape design data due to working accuracy in production of the object to be inspected. Furthermore, in an ultrasonic flaw inspection, the object to be inspected is placed in a predetermined position in the scanner mechanism, but it is difficult to place an object to be inspected having a complicated shape in a predetermined position with high reproducibility.

Another method of generating scanning path information includes a method of driving an ultrasonic transducer with a scanner mechanism on a surface of an object to be inspected, thus teaching and registering each of passage points on an actual scanning path, and generating, as scanning path information, the passage points of the scanner mechanism connected as a scanning path. In this method, the scanner mechanism is driven at each of the passage points on the scanning path to teach and register the scanning path of the scanner mechanism, which requires an enormous amount of time and operation. In particular, if a driving unit provided in the scanner mechanism has a complicated configuration, a very complicated procedure and operation are required.

To perform an ultrasonic flaw inspection with high accuracy, ultrasound transmitted by an ultrasonic transducer needs to be incident on an inspection region of an object to be inspected at a constant angle. For an ultrasonic inspection apparatus that performs a flaw inspection by an aperture synthesis, a constant distance needs to be maintained between an ultrasonic transducer and a surface of an object to be inspected.

Then, an ultrasonic flaw inspection apparatus has been proposed that can hold an object to be inspected and an ultrasonic transducer with a constant distance therebetween, and can cause ultrasound to be incident on the object to be inspected at a constant angle (for example, refer to Japanese Patent Laid-Open Publication No. 63-309852).

The ultrasonic flaw inspection apparatus disclosed in the above Publication includes a distance sensor at a lower end of a drive shaft substantially perpendicular to a scanning stage of a scanner mechanism, and the distance sensor performs scanning on the object to be inspected. Based on measurement data of the distance between the object to be inspected and the distance sensor obtained by scanning, shape data of the object to be inspected that is coordinate data of the scanner mechanism is calculated and stored in a memory. Further, in scanning, scanning path information with each point of the shape data of the object to be inspected as a passage point is prepared and open loop control of a driving mechanism is performed.

An ultrasonic flaw inspection apparatus has been also proposed that considers a deviation from an ideal scanning path that occurs in an ultrasonic flaw inspection. For example, an ultrasonic flaw inspection apparatus has been proposed that uses a distance sensor integrally connected to a probe to perform a shape measurement operation for measuring a shape, and a flaw inspection operation for performing a flaw inspection while performing the shape measurement operation to increase flaw inspection accuracy (for example, refer to Japanese Patent Laid-Open Publication No. 3-77057).

Furthermore, there has been proposed an ultrasonic flaw inspection system that includes an ultrasonic transducer in a scanner mechanism, measures a distance between the ultrasonic transducer and a flaw inspection surface of an object to be inspected, and feeds back the result to control of the scanner mechanism to thereby control the ultrasonic transducer in an optimum position for a flaw inspection (for example, refer to Japanese Patent Laid-Open Publication No. 2005-300363).

The conventional scanner mechanism is used as a driving mechanism that drives an ultrasonic transducer based on ideal scanning path information previously generated, and an adjustment mechanism that adjusts a deviation so that a scanning position of the ultrasonic transducer is located on an ideal scanning path based on a deviation that occurs during an ultrasonic flaw inspection.

However, if the scanner mechanism is used as the driving mechanism and the adjustment mechanism, control of the scanner mechanism becomes complicated, which may reduce accuracy of scanning position control. Thus, in order to maintain control of the scanner mechanism with high accuracy and perform an ultrasonic flaw inspection with high accuracy, it is inevitable to increase scanning time and labor.

DISCLOSURE OF THE INVENTION

The present invention is achieved in view of the above-described circumstances and has an object to provide an ultrasonic inspection apparatus that detects a deviation contained in previously prepared scanning path information and various deviations from an ideal scanning position such as deviations that occur during an ultrasonic flaw inspection and autonomously adjusts the deviations during the ultrasonic flaw inspection to perform an ultrasonic flaw inspection with high accuracy.

In order to achieve the above object, an ultrasonic inspection apparatus according to the present invention includes: an ultrasonic transducer, in which a plurality of piezoelectric transducers are arranged, emits ultrasound to an inspection region of an object to be inspected and receives a reflection echo of the ultrasound; a flaw inspection device that causes the ultrasonic transducer to emit the ultrasound, detects and calculates an electric echo signal of the reflection echo received by the ultrasonic transducer, and generates flaw inspection image information of the inspection region of the object to be inspected; a scanner mechanism that drives the ultrasonic transducer on the object to be inspected based on previously generated scanning path information; a distance and tilt calculation unit that calculates at least one of a distance and a tilt between an opening surface of the ultrasonic transducer and the inspection region of the object to be inspected; a control unit that calculates, based on at least one of the distance and the tilt calculated by the distance and tilt calculation unit, a deviation between a scanning position based on the scanning path information and a predetermined scanning position where a normal line to the inspection region of the object to be inspected and the opening surface of the ultrasonic transducer intersect each other and where the ultrasonic transducer and the inspection region of the object to be inspected are located with a predetermined distance therebetween, and generates a control signal for correcting at least one of the distance and the tilt between the opening surface of the ultrasonic transducer and the inspection region of the object to be inspected to the predetermined scanning position in accordance with the thus calculated deviation; and a driving mechanism that drives the ultrasonic transducer to the predetermined scanning position in response to the control signal generated by the control unit, wherein at least the ultrasonic transducer and the driving mechanism are integrally formed as an integral ultrasonic transducer.

The ultrasonic inspection apparatus according to the present invention can detect various deviations from an ideal scanning position during the ultrasonic flaw inspection and autonomously adjust the deviations to perform an ultrasonic flaw inspection with high accuracy.

BEST MODE FOR CARRYING OUT THE INVENTION

Embodiments of an ultrasonic inspection apparatus according to the present invention will be described with reference to the accompanying drawings.

In the ultrasonic inspection apparatus, an ultrasonic transducer constituted by a piezoelectric conversion unit formed into a matrix array shape or linear array shape scans a surface of an object to be inspected so as to visualize an internal defect, a void, and peeling in the object to be inspected by means of an aperture synthesis technology.

First Embodiment

Figure 1:
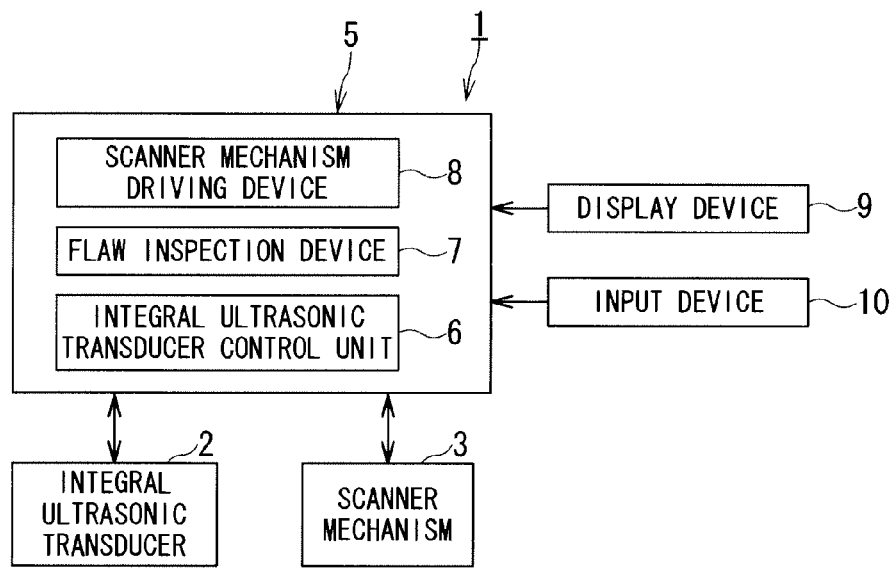
FIG. 1 is a schematic general configuration diagram showing an ultrasonic inspection apparatus according to a first embodiment of the present invention.

FIG. 1 is a schematic general configuration diagram showing an ultrasonic inspection apparatus 1 according to a first embodiment of the present invention.

The ultrasonic inspection apparatus 1 includes an actuator-integrated ultrasonic transducer (hereinafter referred to as an integral ultrasonic transducer) 2, a scanner mechanism 3, and an apparatus body 5 including an integral ultrasonic transducer control device 6, a flaw inspection device 7 and a scanner mechanism driving device 8.

The apparatus body 5 also includes a display device 9 that displays a two or three-dimensional flaw inspection image or the like obtained by an ultrasonic flaw inspection, and an input device 10 that receives inputs concerning various instructions. The display device 9 includes a display unit, a calculation unit, a storage unit, and the like, and can use a flat panel display such as a liquid crystal display, an LED (light emitting diode), an EL (electro luminescence), a VFD (vacuum fluorescence display), a PDP (plasma display panel). The input device 10 may be constituted by a keyboard or a mouse.

Figure 2:
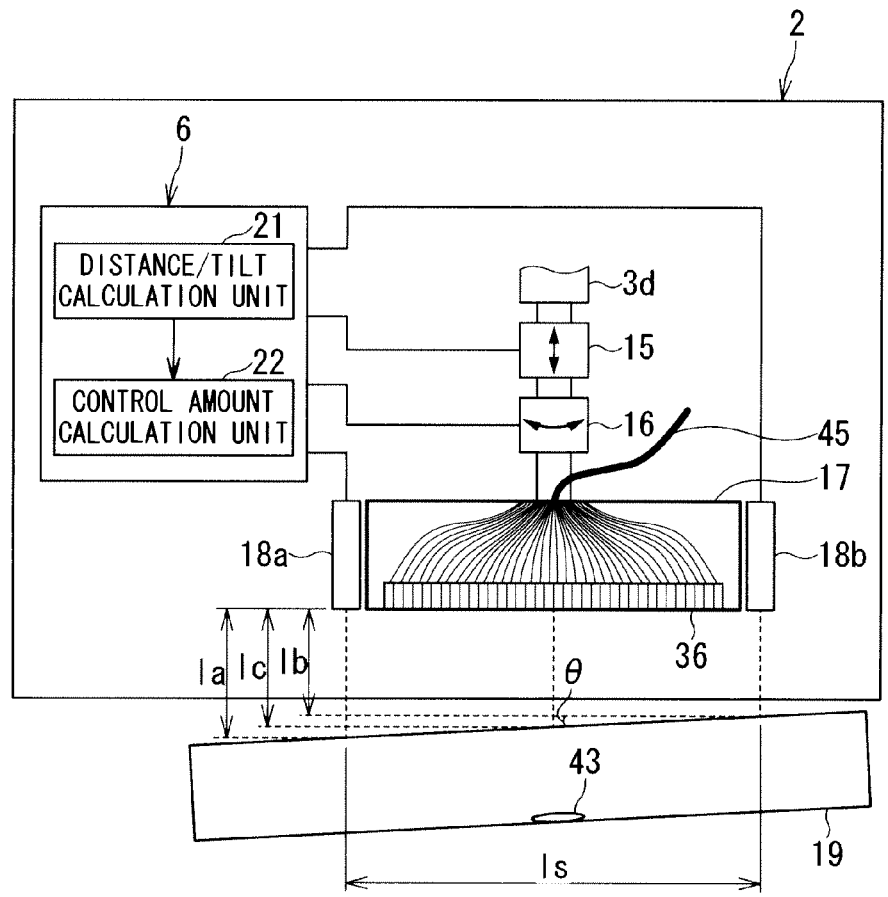
FIG. 2 is a configuration diagram illustrating an integral ultrasonic transducer provided in the ultrasonic inspection apparatus.

FIG. 2 is a configuration diagram illustrating the integral ultrasonic transducer 2 provided in the ultrasonic inspection apparatus 1.

The integral ultrasonic transducer 2 is secured to a YZ drive shaft 3d of the scanner mechanism 3 described later, and a distance controlling actuator 15, a tilt controlling actuator 16 and an ultrasonic transducer 17 are sequentially connected. Distance measuring sensors 18a and 18b are provided at opposite ends in a width direction of the ultrasonic transducer 17. To the distance controlling actuator 15, the tilt controlling actuator 16, and the distance measuring sensors 18a and 18b, the integral ultrasonic transducer control device 6 that controls the actuators 15 and 16 and the sensors 18a and 18b are connected.

The ultrasonic transducer 17 scans an object to be inspected 19 by driving of the distance controlling actuator 15 and the tilt controlling actuator 16 based on control signals transmitted from the integral ultrasonic transducer control device 6 and driving of the scanner mechanism 3.

The distance measuring sensors 18a and 18b are provided in a pair. The distance measuring sensors 18a and 18b use measurement means such as optical measurement means using a laser light or ultrasound measurement means to measure distances la and lb between the object to be inspected 19 and the opposite ends in the width direction of the ultrasonic transducer 17. Measurement results obtained from the distance measuring sensors 18a and 18b are output to the integral ultrasonic transducer control device 6. Further, it is prescribed that a distance is between the distance measuring sensors 18a and 18b is a certain known distance.

The tilt controlling actuator 16 is rotated in an arrow direction around an axis perpendicular to the drawing based on the control signal transmitted from the integral ultrasonic transducer control device 6. The tilt controlling actuator 16 controls a tilt of the ultrasonic transducer 17 with respect to the object to be inspected 19. The distance controlling actuator 15 is driven in an arrow direction along a vertical axis in the drawing based on the control signal transmitted from the integral ultrasonic transducer control device 6. The distance controlling actuator 15 controls a distance between the ultrasonic transducer 17 and the object to be inspected 19.

The scanner mechanism 3 drives the integral ultrasonic transducer 2 on the object to be inspected 19 based on previously generated scanning path information. On the other hand, the distance controlling actuator 15 and the tilt controlling actuator 16 drive the ultrasonic transducer 17 to adjust a deviation of a scanning path based on the control signal transmitted from the integral ultrasonic transducer control device 6.

The integral ultrasonic transducer control device 6 includes a distance and tilt calculation unit 21 and a control amount calculation unit 22.

The distance and tilt (distance/tilt) calculation unit 21 calculates a distance lc between a center of an opening surface of the ultrasonic transducer 17 and the object to be inspected 19 based on the distances la and lb output from the distance measuring sensors 18a and 18b. The distance lc is calculated, for example, by the following expression.

$$lc = (la+lb)/2 \quad \text{[Expression 1]}$$

The distance and tilt calculation unit 21 also calculates a tilt θ of the opening surface of the ultrasonic transducer 17 with respect to the object to be inspected 19 based on the distance lc between the center of the opening surface of the ultrasonic transducer 17 and the object to be inspected 19 calculated by Expression 1. The tilt is calculated, for example, by the following expression.

$$\theta = \tan^{-1}((la-lb)/ls) \quad \text{[Expression 2]}$$

The distance lc and the tilt θ may be calculated by a calculation method other than Expressions 1 and 2.

The control amount calculation unit 22 calculates control amounts of the distance controlling actuator 15 and the tilt controlling actuator 16 based on the calculated distance lc between the center of the opening surface of the ultrasonic transducer 17 and the object to be inspected 19 and the tilt θ of the opening surface of the ultrasonic transducer 17 with respect to the object to be inspected 19. The control amounts of the distance controlling actuator 15 and the tilt controlling actuator 16 are determined so that the ultrasonic transducer 17 is placed in an ideal scanning position where a normal to an inspection region of the object to be inspected 19 and the opening surface of the ultrasonic transducer 17 intersect each other, and the ultrasonic transducer 17 and the inspection region of the object to be inspected 19 are located with a predetermined distance therebetween. The integral ultrasonic transducer control device 6 outputs the control amounts thus obtained to the distance controlling actuator 15 and the tilt controlling actuator 16.

Figure 3:
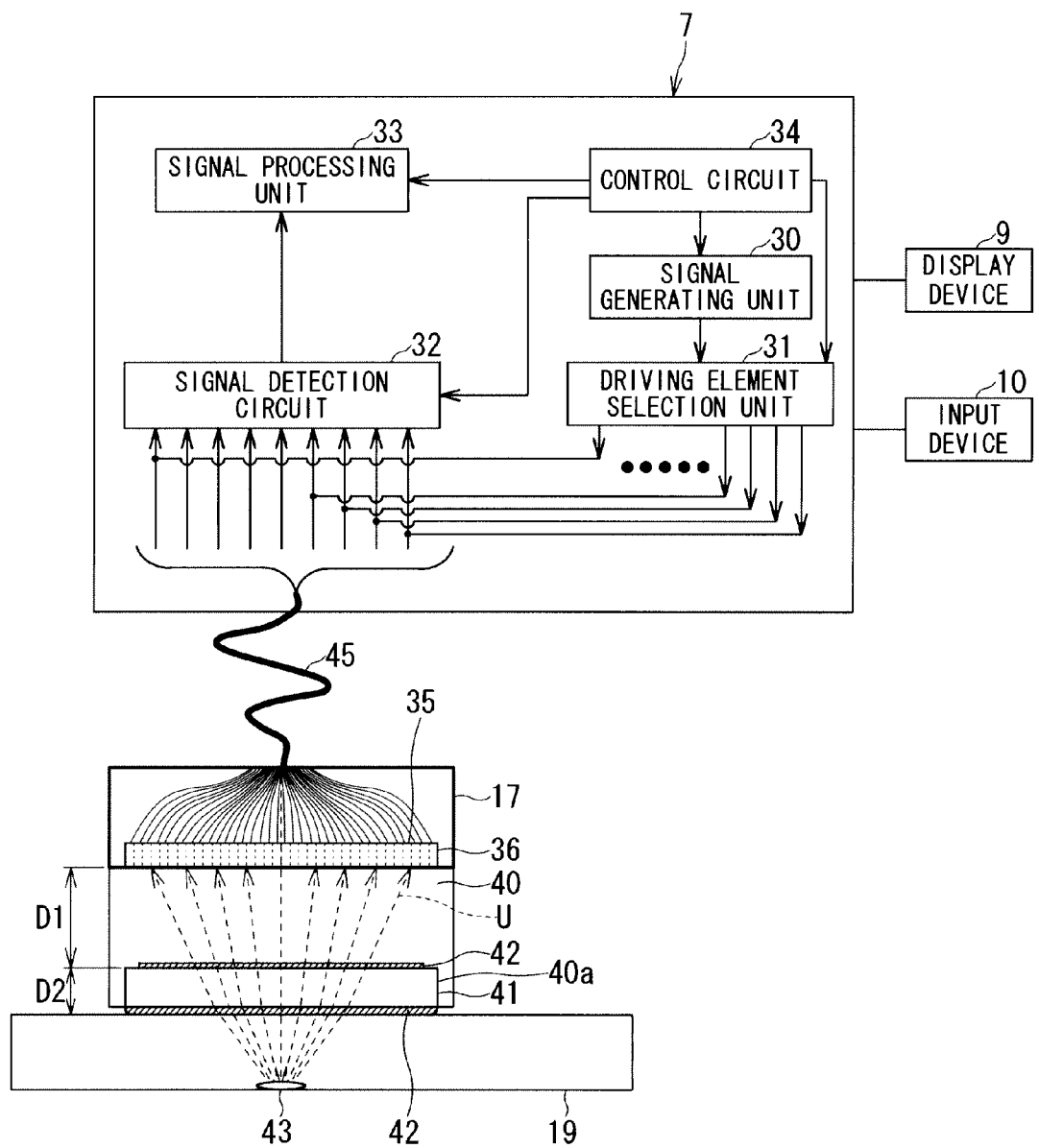
FIG. 3 is a functional configuration diagram illustrating the ultrasonic transducer and a flaw inspection device.

FIG. 3 is a schematic configuration diagram illustrating the ultrasonic transducer 17 that constitutes the integral ultrasonic transducer 2 and the flaw inspection device 7 connected to the ultrasonic transducer 17.

The flaw inspection device 7 includes a signal generation unit 30 that generates a drive signal, a driving element selection unit 31, a signal detection circuit 32, a signal processing unit 33 and a control circuit 34.

The signal generation unit 30 generates a drive signal for driving the ultrasonic transducer 17.

The driving element selection unit 31 selects the drive signal from the signal generation unit 30 and selectively drives piezoelectric transducers or oscillators (piezoelectric conversion elements) 35 in the ultrasonic transducer 17.

In the signal detection circuit 32, ultrasound emitted from the ultrasonic transducer 17 is applied to the inspection region of the object to be inspected 19, and a reflection echo U from the inspection region is detected as an electric echo signal via the ultrasonic transducer 17.

The signal processing unit 33 performs a series of imaging processes such as amplification, A/D conversion, and visualization of the electric echo signal of the reflection echo U detected by the signal detection circuit 32, and generates flaw inspection image information.

The display device 9 includes a display unit, a calculation unit, a storage unit, and the like, and generates and displays a two- or three-dimensional flaw inspection image as required based on flaw inspection image information processed by the signal processing unit 33.

The control circuit 34 controls operations of the signal generation unit 30, the driving element selection unit 31, the signal detection circuit 32, the signal processing unit 33, the display device 9, and the input device 10, and controls a series of operations such as emission and receiving of ultrasound, imaging, and display.

The input device 10 performs instruction inputting to start or finish an inspection or switch an image, or setting inputting of an inspection condition into the control circuit 34 and causes an operation of the ultrasonic inspection apparatus 1.

Hereunder, the ultrasonic transducer 17 will be described.

The ultrasonic transducer 17 includes a piezoelectric conversion unit 36 in which the multiple piezoelectric transducers 35 as the piezoelectric conversion elements are arranged in an m×n matrix. The piezoelectric conversion unit 36 constitutes an ultrasonic sensor that is a matrix sensor.

The drive signal generated by the signal generation unit 30 is selected by the driving element selection unit 31 and added to each of the piezoelectric transducers 35 in the ultrasonic transducer 17. A driving order of each or plural number of the piezoelectric transducers 35 is determined by the selection by the driving element selection unit 31, and each piezoelectric transducer 35 is driven at required driving timing so as to emit ultrasound.

The ultrasound emitted by each piezoelectric transducer 35 is applied to the inspection region of the object to be inspected 19, and a part of the ultrasound is reflected from a density boundary layer of the inspection region to be the reflection echo U. The reflection echo U is received by the ultrasonic transducer 17 (matrix sensor) that is an ultrasound sensor.

A shoe member 40 that is a solid acoustic propagation medium is bonded to a side of an emitting and receiving surface that is an ultrasonic sensor surface of the ultrasonic transducer 17, specifically, a side of the object to be inspected 19. The shoe member 40 includes a soft shoe insertion portion 40a that is a hollow portion formed by hollowing out a surface of the shoe member 40 in contact with the object to be inspected 19, for example, in a flat plate shape. A soft shoe 41 made of relatively low-attenuation rubber such as silicone rubber is fitted into the soft shoe insertion portion 40a of the shoe member 40.

The soft shoe 41 is formed of a member softer than the shoe member 40 and is hence easily deformed according to a shape of a contact surface of the object to be inspected 19. The soft shoe 41 has substantially the same shape as that of the soft shoe insertion portion. Thus, the soft shoe 41 is bonded and secured so as to be able to partially protrude from the hollow portion in the shoe member 40. The soft shoe 41 deteriorates earlier than the shoe member 40 and is thus removably formed to be replaceable.

A thickness D1 of the shoe member 40 and a thickness D2 of the soft shoe 41 are determined based on a sound speed ratio between the shoe member 40 and the soft shoe 41. Specifically, the thickness D1 of the shoe member 40 and the thickness D2 of the soft shoe 41 are determined so that a ratio between the thicknesses D1 and D2 is the sound speed ratio between the shoe member 40 and the soft shoe 41. Thus, multiple echoes obtained from the object to be inspected 19 are superimposed to optimize a depth that can be inspected.

A low-volatile gel-like liquid couplant 42 is provided on a contact surface between the shoe member 40 and the object to be inspected 19 and the soft shoe 41 for acoustic matching of ultrasound. The shoe member 40 is bonded and secured to the contact surface of the object to be inspected 19 via the liquid couplant 42. The soft shoe 41 is removably fitted into the soft shoe insertion portion 40a via the liquid couplant 42.

The ultrasound successively emitted from the respective piezoelectric transducers 35 in the ultrasonic transducer 17 sequentially passes through the shoe member 40 as the acoustic propagation medium, the liquid couplant 42, the soft shoe 41 and the liquid couplant 42, is incident on the inspection region of the object to be inspected 19, and is reflected by boundary layers of the inspection region.

The reflection echo U of the ultrasound reflected by the boundary layers such as the surface of the object to be inspected 19, a boundary surface, a bottom surface, or an internal defect 43 passes from the object to be inspected 19 sequentially through the liquid couplant 42, the soft shoe 41, the liquid couplant 42 and the shoe member 40, and is received by the piezoelectric transducers 35 of the ultrasonic transducer 17 with time differences. The reflection echo U oscillates the piezoelectric transducers 35 and is converted into an electric signal (electric echo signal). The electric echo signal is then input to the signal detection circuit 32 via a signal cable 45 and detected for each piezoelectric transducer 35.

The signal detection circuit 32 is connected in alignment to each piezoelectric transducer 35 in the ultrasonic transducer 17 via the signal cable 45. The electric echo signal generated by each piezoelectric transducer 35 of the piezoelectric conversion unit 36 is guided to the signal detection circuit 32 via the signal cable 45. A drive signal from the signal generation unit 30 is guided to each piezoelectric transducer 35 of the piezoelectric conversion unit 36 via the driving element selection unit 31 using the signal cable 45.

An operation of the flaw inspection device 7 of the ultrasonic inspection apparatus 1 will be described hereunder.

When the drive signal is applied to a piezoelectric transducer 35 in the m-th row and n-th column among the piezoelectric transducers 35 in the ultrasonic transducer 17, the piezoelectric transducer 35 operates to generate ultrasound as a piezoelectric body and emits the ultrasound. The emitted ultrasound passes through the shoe member 40, the soft shoe 41 and the liquid couplant 42 and is applied to the inspection region of the object to be inspected 19. At this time, the ultrasound is applied to the inspection region of the object to be inspected 19 at a constant angle and with a constant distance.

The ultrasound applied to the inspection region of the object to be inspected 19 is partially reflected by the density boundary layer of the inspection region to be the reflection echo U. The reflection echo U passes through the liquid couplant 42, the soft shoe 41, and the shoe member 40 and is returned to the ultrasonic transducer 17, and received by the piezoelectric transducers 35 with time differences. The reflection echo U is converted into an electric echo signal by a piezoelectric conversion by the piezoelectric transducers 35, and the signal is transmitted to the signal detection circuit 32 via the signal cable 45 and detected.

A plurality of electric echo signals required for an inspection among electric echo signals detected by the signal detection circuit 32 are guided to the signal processing unit 33. The signal processing unit 33 performs a series of processes such as amplification, A/D conversion, and visualization of the guided electric echo signals, and generates flaw inspection image information. The generated flaw inspection image information is guided to the display device 9 and imaged, and a two- or three-dimensional flaw inspection image is displayed.

Figure 4:
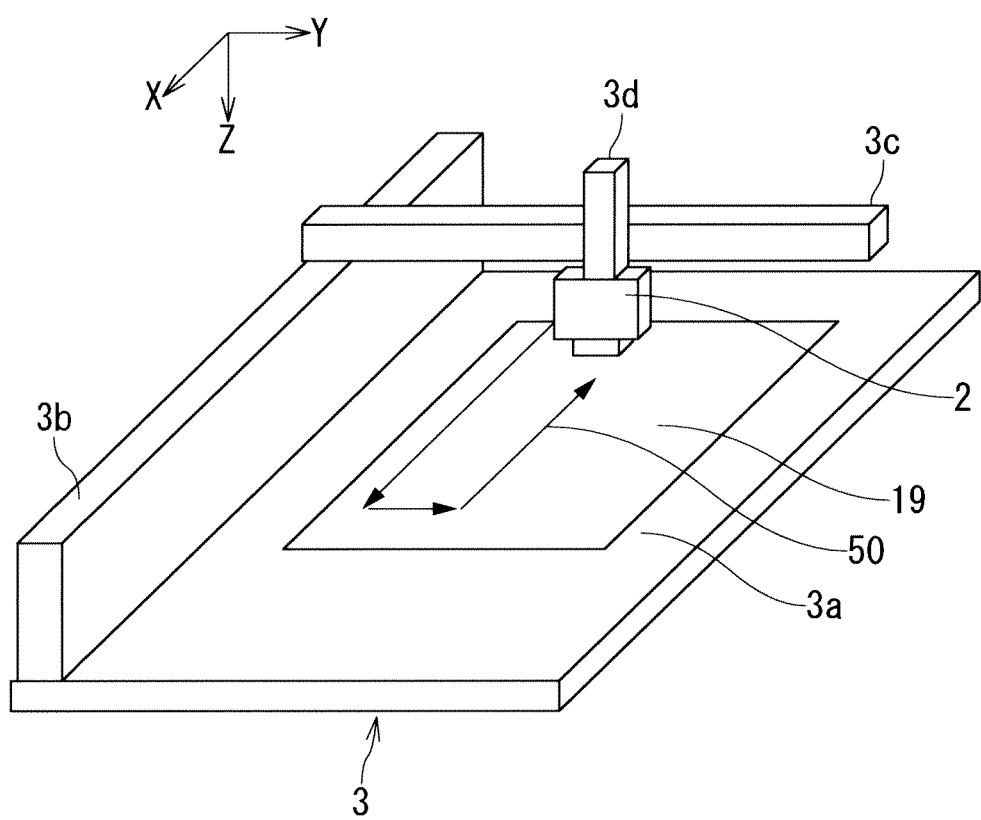
FIG. 4 is a configuration diagram for explaining a scanner mechanism in the first embodiment.

FIG. 4 is a configuration diagram illustrating the scanner mechanism 3.

The scanner mechanism 3 includes a scanning stage 3a on which the object to be inspected 19 is placed, a securing portion 3b substantially vertically secured to one side of the scanning stage 3a, an X-axis driving portion 3c driven on the securing portion 3b in an X-axis direction, and a YZ-axis driving portion 3d driven in Y-axis and Z-axis directions. At a lower end of the YZ-axis driving portion 3d, the integral ultrasonic transducer 2 in FIG. 2 is formed. The X-axis driving portion 3c and the YZ-axis driving portion 3d of the scanner mechanism 3 are driven in the X-axis, Y-axis and Z-axis directions based on control signals transmitted from the scanner mechanism driving device 8 of the apparatus body 5. The X-axis, the Y-axis and the Z-axis intersect each other. The scanning stage 3a may be omitted from the scanner mechanism 3 by the securing portion 3b being directly secured to the object to be inspected 19.

The object to be inspected 19 is placed on the scanning stage 3a of the scanner mechanism 3. The integral ultrasonic transducer 2 scans the surface of the object to be inspected 19 according to driving of the X-axis driving portion 3c and the YZ-axis driving portion 3d. For the integral ultrasonic transducer 2 to scan the surface of the object to be inspected 19, scanning path information 50 needs to be previously prepared.

The scanning path information 50 is information on a path along which the integral ultrasonic transducer 2 secured to the lower end of the YZ-axis driving portion 3d of the scanner mechanism moves to scan the object to be inspected 19. The scanning path information 50 is shown by arrows in the X-axis and Y-axis directions on the object to be inspected 19 in FIG. 4.

The scanning path information 50 is information on a path for a combination of movements of scanning a required length in the X-axis direction perpendicular to an opening width of the ultrasonic transducer, then shifting in the Y-axis direction by the opening width of the ultrasonic transducer, and scanning a required length in the opposite X-axis direction.

The scanner mechanism driving device 8 drives the X-axis driving portion 3c and the YZ-axis driving portion 3d based on the scanning path information 50. Thus, the integral ultrasonic transducer 2 automatically moves on and scans the object to be inspected 19.

The scanning path information 50 is generated by a method of preparing the information using computer software based on shape design data of the object to be inspected 19, or a method of actually driving the scanner mechanism 3 to teach and register each passage point on the scanning path. In order that the ultrasound can be incident on the inspection region of the object to be inspected 19 under a substantially constant condition, the scanning path information 50 is generated so that the normal line to the inspection region of the object to be inspected 19 and the opening surface of the ultrasonic transducer 17 intersect each other, and a distance between the opening surface of the ultrasonic transducer 17 and the surface of the object to be inspected 19 becomes constant. However, there exist factors for various deviations such as a deviation that occurs during generation of the scanning path information 50, or a deviation in placement of the object to be inspected 19 on the scanner mechanism 3.

To address these various deviations, the ultrasonic inspection apparatus 1 of this embodiment performs an ultrasonic flaw inspection while performing a deviation correction process using the integral ultrasonic transducer 2 integrally including the distance controlling actuator 15, the tilt controlling actuator 16, and the distance measuring sensors 18a and 18b. The integral ultrasonic transducer 2 detects a deviation from an ideal scanning position. The integral ultrasonic transducer 2 absorbs the deviation in real time using the distance controlling actuator 15 and the tilt controlling actuator 16 and thus autonomously adjusts the deviation and can perform an ultrasonic flaw inspection with high accuracy.

Figure 5:
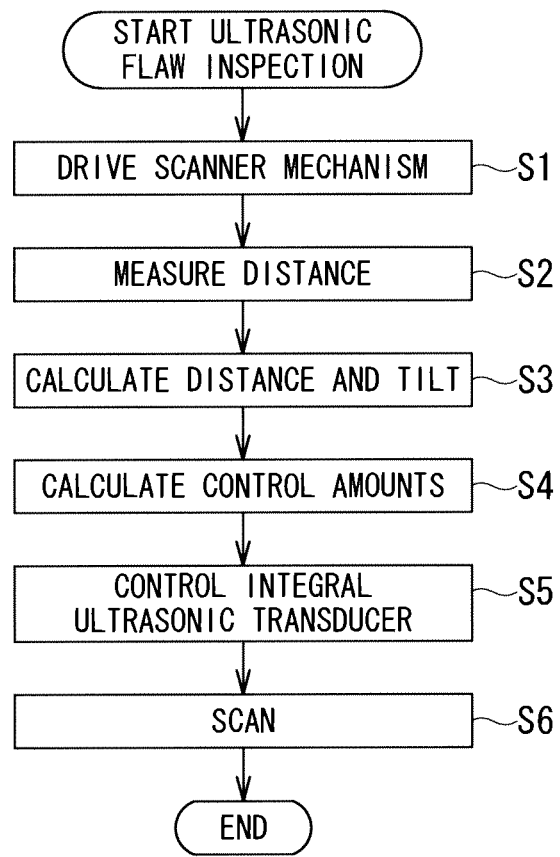
FIG. 5 is a flowchart illustrating a flow of an ultrasonic flaw inspection including a deviation correction process.

The ultrasonic flaw inspection including the deviation correction process using the ultrasonic inspection apparatus 1 of this embodiment will be described hereunder with reference to FIG. 5.

The ultrasonic flaw inspection using the ultrasonic inspection apparatus 1 is applicable to an object to be inspected 19 having various shapes such as a flat shape, a cylindrical shape or a spherical shape and an object 19 made of, for example, a metal material or a resin material. The ultrasonic flaw inspection may be applied to an object to be inspected 19 made of a single material and also a multilayer structure including two or more structures stacked and welded.

In the ultrasonic flaw inspection using the ultrasonic inspection apparatus 1, the object to be inspected 19 is placed on the scanning stage 3a of the scanner mechanism 3. The ultrasonic flaw inspection is started, for example, based on an instruction to start an inspection input by the input device 10.

In step S1, the scanner mechanism driving device 3 drives the X-axis driving portion 3c and the YZ-axis driving portion 3d of the scanner mechanism 3 on the object 19 placed on the scanning stage 3a based on the previously generated scanning path information 50.

In step S2, the distance measuring sensors 18a and 18b use measurement means such as optical measurement using a laser light or ultrasound measurement to measure distances la and lb from the object to be inspected 19. A measurement result is output to the distance and tilt calculation unit 21 in the integral ultrasonic transducer control device 6.

In step S3, the distance and tilt calculation unit 21 in the integral ultrasonic transducer control device 6 calculates a distance lc between the center of the opening surface of the ultrasonic transducer 17 and the object to be inspected 19 based on the distances la and lb measured in the distance measurement step S2 by Expression 1.

The distance and tilt calculation unit 21 also calculates a tilt θ of the opening surface of the ultrasonic transducer 17 with respect to the object to be inspected 19 based on the calculated distance lc by Expression 2.

In step S4, the control amount calculation unit 22 in the integral ultrasonic transducer control device 6 calculates control amounts of the distance controlling actuator 15 and the tilt controlling actuator 16 based on the distance lc and the tilt θ calculated in the distance and tilt (distance/tilt) calculation step S3. The calculated control amounts are output to the distance controlling actuator 15 and the tilt controlling actuator 16. The control amounts of the distance controlling actuator 15 and the tilt controlling actuator 16 are determined so that the ultrasonic transducer 17 is placed in an ideal scanning position where the normal line to the inspection region of the object to be inspected 19 and the opening surface of the ultrasonic transducer 17 intersect each other, and the opening surface of the ultrasonic transducer 17 and the inspection region of the object to be inspected 19 take a predetermined distance therebetween.

In step S5, the distance controlling actuator 15 and the tilt controlling actuator 16 are moved or rotated based on the control amounts calculated in the control amount calculation step S4. Thus, the ultrasonic transducer 17 is placed in an ideal scanning position.

In step S6, the ultrasonic transducer 17 in the integral ultrasonic transducer 2 scans the inspection region of the object to be inspected 19. The ultrasonic transducer 17 moves on and scans the surface of the object to be inspected 19 based on the control performed by the flaw inspection device 7 in the apparatus body 5. The flaw inspection device 7 performs a series of processes such as amplification, A/D conversion, and visualization of an electric echo signal of a reflection echo obtained by the scanning process to thereby generate flaw inspection image information. The generated flaw inspection image information is guided to the display device 9 and then imaged, and a two- or three-dimensional flaw inspection image is displayed. The ultrasonic flaw inspection is thus finished.

The deviation correction process of the scanning path information from the distance measurement step S2 to the control step S5 is performed in real time simultaneously with the movement of the integral ultrasonic transducer 2.

The scanner mechanism 3 is driven based on the previously generated scanning path information 50 to move the integral ultrasonic transducer 2. Furthermore, the scanner mechanism 3 is driven based on the deviations detected using the distance controlling actuator 15 and the tilt controlling actuator 16 to move the ultrasonic transducer 17 to the ideal scanning position. This allows an ultrasonic flaw inspection to be performed with high accuracy without complicated control of the scanner mechanism 3. The deviation correction process of the scanning path information is performed at a start of the ultrasonic flaw inspection or at a certain cycle during the ultrasonic flaw inspection, thereby reducing a working time of the ultrasonic flaw inspection and increasing working efficiency.

With the ultrasonic inspection apparatus 1, the integral ultrasonic transducer 2 includes the distance measuring sensors 18a and 18b, the distance controlling actuator 15, and the tilt controlling actuator 16, and thus a deviation between the ideal scanning position and an actual scanning position can be detected. Thus, even if there is a deviation in the scanning path of the scanner mechanism 3 driven based on the previously generated scanning path information 50 during the ultrasonic flaw inspection, the deviation can be absorbed in real time and autonomously adjusted, thereby allowing an ultrasonic flaw inspection to be performed with high accuracy.

Furthermore, the ultrasonic inspection apparatus 1 detects a deviation between the ideal scanning position and the scanning position based on the scanning path information 50 and can absorb the deviation in the distance controlling actuator 15 and the tilt controlling actuator 16. Thus, the ultrasonic inspection apparatus 1 can perform finer deviation correction, the normal line to the inspection region of the object to be inspected 19 and the opening surface of the ultrasonic transducer 17 intersect each other, and a constant distance can be maintained between the center of the opening surface of the ultrasonic transducer 17 and the surface of the object to be inspected 19. This allows an ultrasonic flaw inspection to be performed with high accuracy.

Further, the acoustic propagation medium constituted by the shoe member 40 into which the soft shoe 41 is inserted is used to improve followability to shape changes of the inspection region of the object to be inspected 19, and prevent entry of bubbles, improving performance of the ultrasonic flaw inspection. The soft shoe 41 that early deteriorates is replaceable, thereby improving maintainability of the ultrasonic inspection apparatus 1. Furthermore, the thickness D1 of the shoe member 40 and the thickness D2 of the soft shoe 41 are determined based on the sound speed ratio between the shoe member 40 and the soft shoe 41, and thus, the multiple echoes from the object to be inspected 19 are superimposed to thereby optimize a depth that can be inspected.

Although, as an example of the object to be inspected 19, the flat-shaped object to be inspected 19 is described, the object is not limited thereto, and the object to be inspected 19 may have other shapes such as a spherical or cylindrical shape.

In the scanner mechanism 3, rotating portions that are rotated around rotation axes in the X-axis direction, the Y-axis direction and the Z-axis direction may be provided, respectively. Besides the distance controlling actuator 15 and the tilt controlling actuator 16 provided in the integral ultrasonic transducer 2, another controlling actuator driven in a different direction may be provided.

Further, the integral ultrasonic transducer 2 may include therein or externally the integral ultrasonic transducer control device 6.

Furthermore, although the acoustic propagation medium constituted by the shoe member 40 into which the soft shoe 41 is inserted is used, the medium is not limited thereto, and an acoustic propagation medium constituted by a shoe member 40 alone may be used.

The deviation correction process for the distance lc between the center of the opening surface of the ultrasonic transducer 17 and the object to be inspected 19 and the tilt θ of the opening surface of the ultrasonic transducer 17 with respect to the object to be inspected 19 is performed using the distance controlling actuator 15 and the tilt controlling actuator 16. However, the deviation correction process may be performed for one of the distance lc and the tilt θ according to the shape of the object to be inspected 19. For example, in the case where the object to be inspected 19 has a flat shape, only the distance controlling actuator 15 may be provided to correct only the distance, thereby achieving an ultrasonic flaw inspection with high accuracy. Such a configuration can also simplify a configuration of the ultrasonic inspection apparatus.

Furthermore, the group of transducers in the ultrasonic transducer 2 in the matrix array shape may be arranged in a linear shape, a honeycomb shape, a concentric circular shape, or a triangular shape without being limited to the matrix shape. The group of transducers may be three-dimensionally arranged. In the piezoelectric conversion unit 36, the piezoelectric transducers 35 may be arranged in a line or a cross line (array) instead of the matrix shape to form an array sensor.

Further in this embodiment, although the two distance measuring sensors 18a and 18b are provided in one pair at the opposite ends in the width direction of the ultrasonic transducer 17, the distance measuring sensors 18a and 18b may be provided close to the ultrasonic transducer 17. A set of two or more, for example, three distance measuring sensors 18a and 18b may be provided.

Second Embodiment

An ultrasonic inspection apparatus according to a second embodiment of the present invention will be described hereunder.

Figure 6:
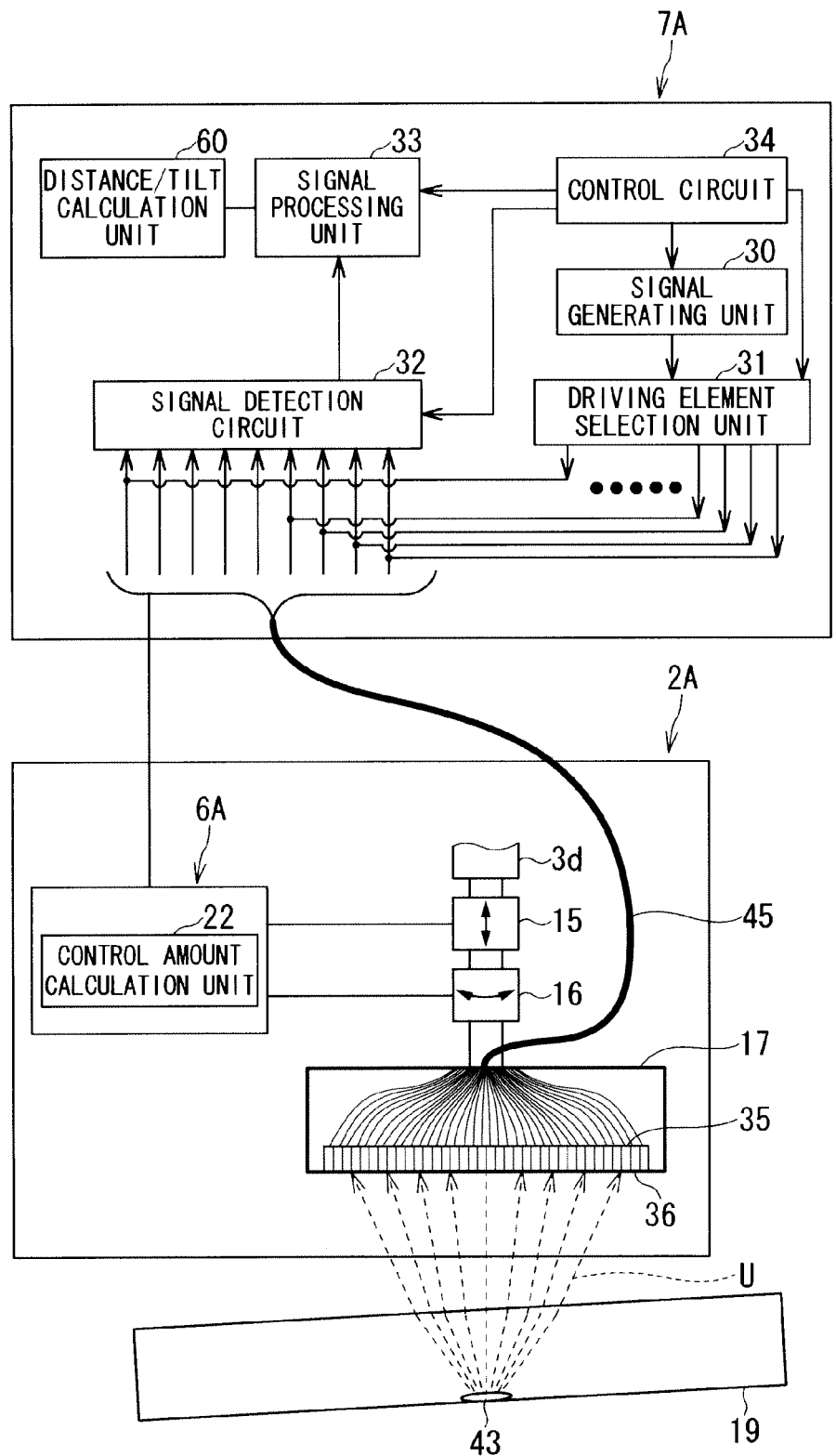
FIG. 6 is a schematic configuration diagram of an integral ultrasonic transducer and a flaw inspection device of an ultrasonic inspection apparatus according to a second embodiment of the present invention.

FIG. 6 is a schematic configuration diagram of an integral ultrasonic transducer 2A and a flaw inspection device 7A of the ultrasonic inspection apparatus according to the second embodiment of the present invention.

The ultrasonic inspection apparatus of the second embodiment is different from the ultrasonic inspection apparatus 1 of the first embodiment in that a distance and a tilt between an opening surface of an ultrasonic transducer and an inspection region of an object to be inspected are calculated based on flaw inspection image information obtained by a flaw inspection device 7A. Configurations and components corresponding to those of the first embodiment are denoted by the same reference numerals, and overlapping descriptions will be omitted herein.

The flaw inspection device 7A connected to an ultrasonic transducer 17 includes a distance and tilt calculation unit 60 in addition to the configuration of the flaw inspection device 7 in FIG. 2. The distance and tilt calculation unit 60 calculates a distance lc between a center of an opening surface of the ultrasonic transducer 17 and an inspection region of an object to be inspected 19 from a flaw inspection image information generated by a signal processing unit 33 performing a series of imaging processes such as amplification, A/D conversion, and visualization of an electric echo signal obtained from a reflection echo U detected by a signal detection circuit 32.

The distance and tilt calculation unit 60 also calculates a tilt θ between the opening surface of the ultrasonic transducer 17 and an opposing flaw inspection surface of the object to be inspected 19. The distance lc and the tilt θ between the opening surface of the ultrasonic transducer 17 and the flaw inspection surface of the object to be inspected 19 can be calculated when a deviation is within a certain range from previously generated scanning path information of the ultrasonic transducer 17, and the deviation can be obtained from the image flaw inspection information.

The flaw inspection image information generated by the signal processing unit 33 is two- or three-dimensional image information. The flaw inspection image information includes distance information from the inspection region of the object to be inspected 19 obtained from each piezoelectric conversion unit 36 in the ultrasonic transducer 17, and from such distance information, the distance lc and the tilt θ between the ultrasonic transducer 17 and the object to be inspected 19 can be obtained.

The flaw inspection device 7A is connected to an integral ultrasonic transducer control device 6A. The distance lc and the tilt θ between the ultrasonic transducer 17 and the inspection region of the object to be inspected 19 calculated by the distance and tilt calculation unit 60 in the flaw inspection device 7A are output to the integral ultrasonic transducer control device 6A. In the integral ultrasonic transducer control device 6A, the control amount calculation unit 22 calculates control amounts of a distance controlling actuator 15 and a tilt controlling actuator 16 based on the distance lc and the tilt θ output from the flaw inspection device 7A.

The control amounts of the distance controlling actuator 15 and the tilt controlling actuator 16 calculated by the control amount calculation unit 22 are output as control signals to the distance controlling actuator 15 and the tilt controlling actuator 16, respectively. The control actuators 15 and 16 are driven based on the control signals.

Figure 7:
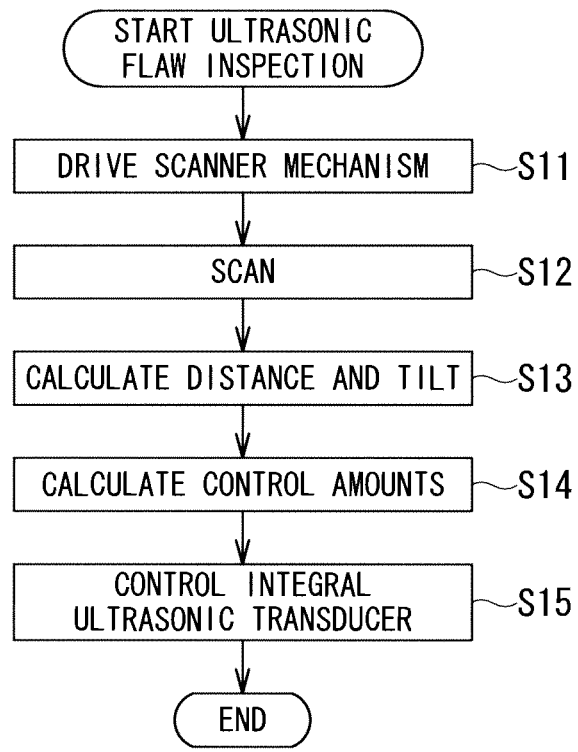
FIG. 7 is a flowchart illustrating a flow of an ultrasonic flaw inspection including a deviation correction process in the second embodiment.

An ultrasonic flaw inspection including a deviation correction process using the ultrasonic inspection apparatus of this embodiment will be described with reference to FIG. 7. In the ultrasonic flaw inspection using the ultrasonic inspection apparatus, the object to be inspected 19 is placed on a scanning stage 3a of a scanner mechanism 3, and the ultrasonic flaw inspection is started, for example, based on an instruction to start an inspection input by an input device 10.

In step S11, the scanner mechanism driving device 3 drives an X-axis driving portion 3c and a YZ-axis driving portion 3d of the scanner mechanism 3 on the object to be inspected 19 placed on the scanning stage 3a based on previously generated scanning path information 50.

In step S12, the ultrasonic transducer 17 of the integral ultrasonic transducer 2A scans the inspection region of the object to be inspected 19. The ultrasonic transducer 17 moves on and scans the surface of the object to be inspected 19 based on the control performed by the flaw inspection device 7A in an apparatus body 5. The flaw inspection device 7A performs a series of processes such as amplification, A/D conversion, and visualization of an electric echo signal of a reflection echo obtained by scanning, and the signal processing unit 33 generates the flaw inspection image information.

In step S13, the distance and tilt calculation unit 60 calculates the distance lc between the center of the opening surface of the ultrasonic transducer 17 and the inspection region of the object to be inspected 19 from the flaw inspection image information generated by the signal processing unit 33. The distance and tilt calculation unit 60 also calculates a tilt θ between the opening surface of the ultrasonic transducer 17 and the opposing flaw inspection surface of the object to be inspected 19. The distance lc and the tilt θ between the ultrasonic transducer 17 and the inspection region of the object to be inspected 19 calculated by the distance and tilt calculation unit 60 are output to the integral ultrasonic transducer control device 6A.

In step S14, the control amount calculation unit 22 in the integral ultrasonic transducer control device 6A calculates control amounts of the distance controlling actuator 15 and the tilt controlling actuator 16 based on the distance lc and the tilt θ output from the flaw inspection device 7A. The control amounts calculated by the control amount calculation unit 22 are output as control signals to the distance controlling actuator 15 and the tilt controlling actuator 16, respectively.

In step S15, the distance controlling actuator 15 and the tilt controlling actuator 16 are driven based on the control amounts calculated by the control amount calculation unit 22. Thus, the integral ultrasonic transducer 2A is placed in an ideal scanning position. The integral ultrasonic transducer 2A placed in the ideal scanning position performs scanning as in the scanning step S12.

With the ultrasonic inspection apparatus, in addition to the advantageous effect achieved by the ultrasonic inspection apparatus of the first embodiment, the distance lc and the tilt θ between the ultrasonic transducer 17 and the flaw inspection surface of the object to be inspected 19 can be detected without using the distance measuring sensors 18a and 18b, thus simplifying the apparatus and improving the productivity of the ultrasonic inspection apparatus.

Third Embodiment

An ultrasonic inspection apparatus according to a third embodiment of the present invention will be described hereunder.

The ultrasonic inspection apparatus of the third embodiment is different from the ultrasonic inspection apparatus of the second embodiment in that an ultrasonic transducer 17B in an integral ultrasonic transducer 2B is provided on an arc, and the ultrasonic inspection apparatus is used for an ultrasonic flaw inspection of an inspection region of an object to be inspected 19B having inner and outer surfaces of a corner portion such as a pipe.

Figure 8:
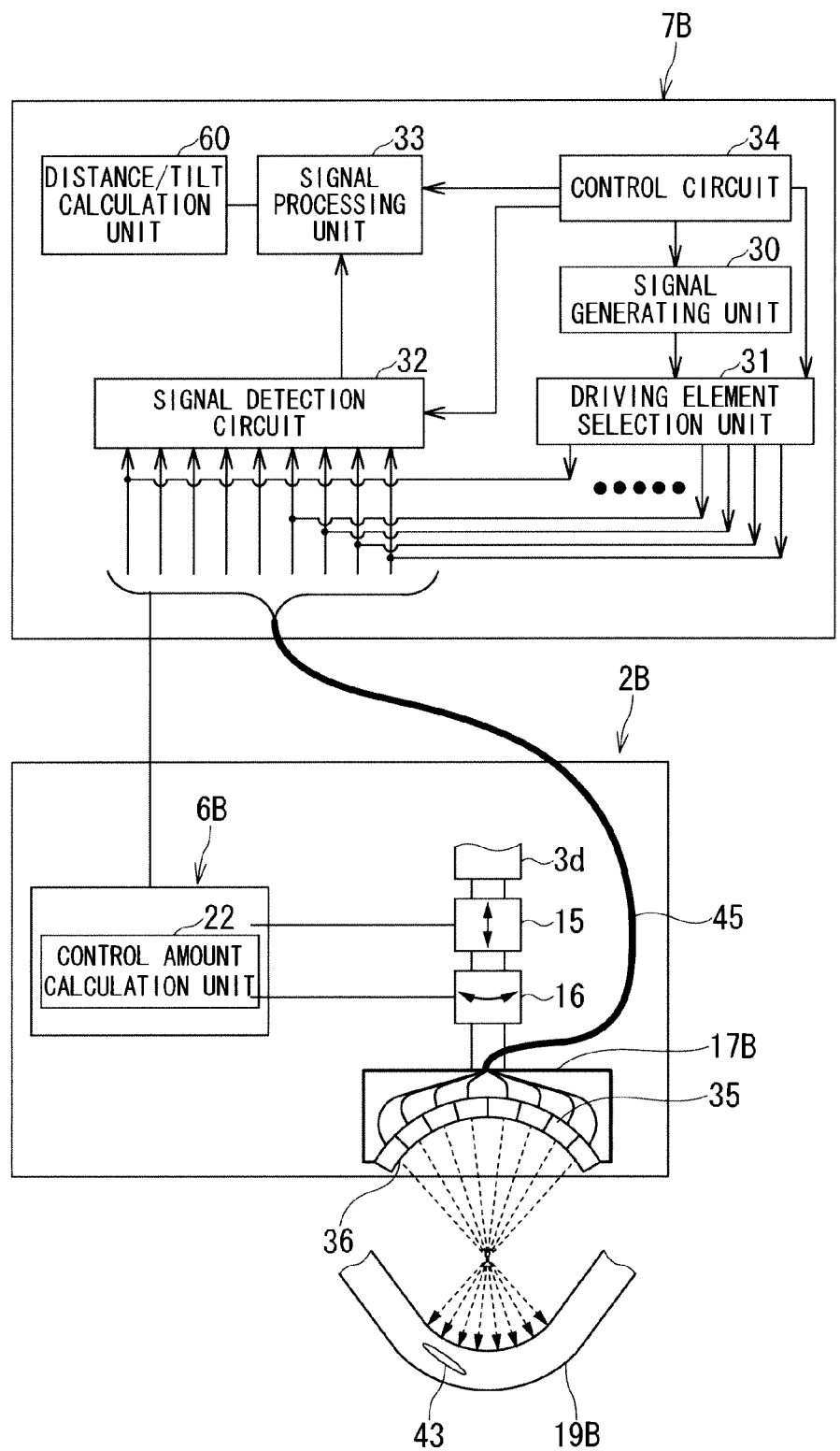
FIG. 8 is a schematic configuration diagram of an integral ultrasonic transducer and a flaw inspection device of an ultrasonic inspection apparatus according to a third embodiment of the present invention.

FIG. 8 is a schematic configuration diagram of the integral ultrasonic transducer 2B and the flaw inspection device 7B of the ultrasonic inspection apparatus according to the third embodiment of the present invention. Configurations and components corresponding to those in the first and second embodiments are denoted by the same reference numerals, and overlapping descriptions will be omitted herein.

The ultrasonic transducer 17B in the integral ultrasonic transducer 2B includes a piezoelectric conversion unit 36 in which piezoelectric transducers 35 are arranged in an arcuate shape. In an actual ultrasonic flaw inspection time, the ultrasonic transducer 17B is placed in a position where a center of curvature of an arc of the arranged piezoelectric transducers 35 substantially accords with a center of curvature of an arc of a corner portion surface that is the inspection region of the object to be inspected 19B for scanning. The ultrasonic transducer 17B is placed in this manner, thus emitting the ultrasound from each piezoelectric transducer 35 with a constant distance being maintained between a center of an opening surface of the ultrasonic transducer 17B and the corner portion surface of the object to be inspected 19B. This allows an image similar to an image obtained in a flaw inspection of a flat surface to be obtained.

The flaw inspection device 7B includes a distance and tilt calculation unit 60. The distance and tilt calculation unit 60 calculates a distance and a tilt between the ultrasonic transducer 17B and the flaw inspection surface of the object to be inspected 19B. The distance and the tilt are detected based on an reflection echo that is an amplified electric signal detected by the signal detection circuit 32 in the signal processing unit 33, or flaw inspection image information generated by the signal processing unit 33 performing a series of imaging processes such as A/D conversion and visualization.

Figure 9:
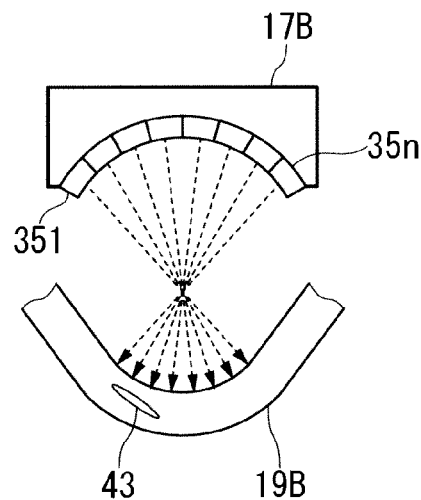
FIG. 9(A) shows a case where the ultrasonic transducer and an object to be inspected are held in an appropriate scanning position.
FIG. 9(B) shows a distance D between each piezoelectric transducer and an inspection region of the object to be inspected obtained from a reflection echo of the piezoelectric transducer.
Figure 9:
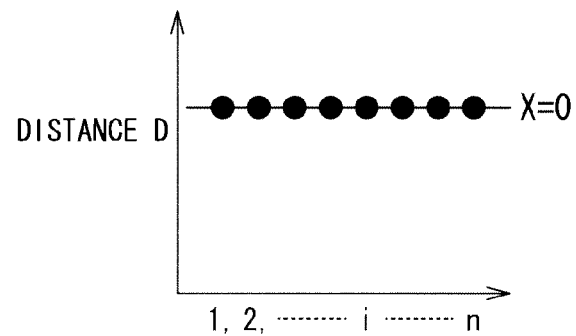
Figure 10:
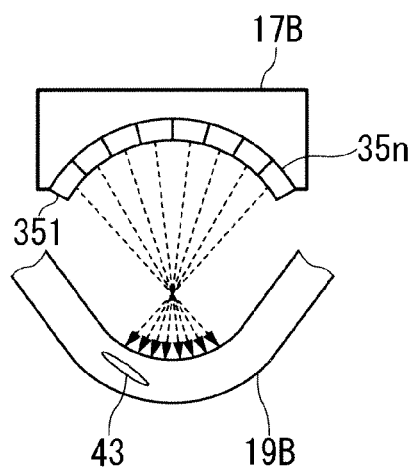
FIG. 10(A) shows a case where the ultrasonic transducer and the object to be inspected are held in positions close to each other.
FIG. 10(B) shows a distance D between each piezoelectric transducer and the inspection region of the object to be inspected obtained from a reflection echo of the piezoelectric transducer.
Figure 10:
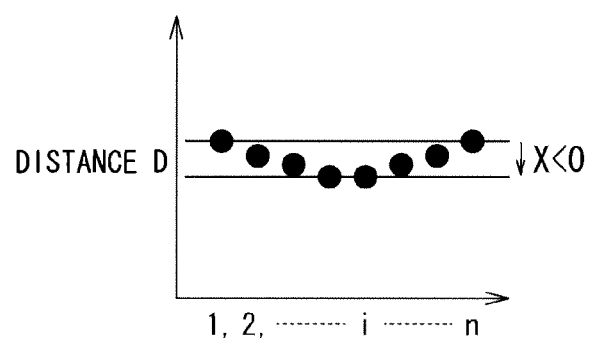
Figure 11:
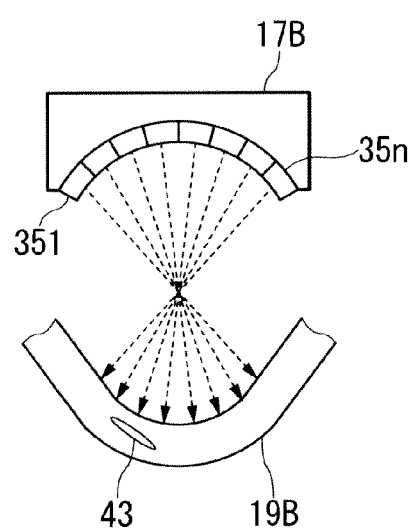
FIG. 11(A) shows a case where the ultrasonic transducer and the object to be inspected are held in positions away from each other.
FIG. 11(B) shows a distance D between each piezoelectric transducer and the inspection region of the object to be inspected obtained from a reflection echo of the piezoelectric transducer.
Figure 11:
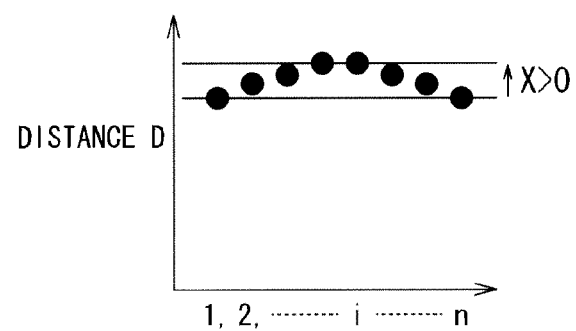

Herein, in the deviation correction process, there will be described the case where the distance and tilt calculation unit 60 calculates the distance and the tilt between the ultrasonic transducer 17B and the flaw inspection surface of the object to be inspected 19B from the reflection echo FIGS. 9 to 11 show an example of a distance D between each piezoelectric transducer 35 and the inspection region of the object to be inspected 19B obtained from a reflection echo of each of n piezoelectric transducers 351, 352, . . . 35i, 35n (hereinafter referred to as piezoelectric transducers 35) arranged in the piezoelectric conversion unit 36. In FIGS. 9(B), 10(B) and 11(B), the abscissa represents the piezoelectric transducers 35, and the ordinate represents the distance D between the piezoelectric transducers 35 and the inspection region of the object to be inspected 19B. A maximum difference X is a difference between a distance between the piezoelectric transducer 35 located at substantially the center and the inspection region of the object to be inspected 19B and a distance between each of the piezoelectric transducers 351 and 35n located at opposite ends and the inspection region of the object to be inspected 19B.

FIG. 9(A) shows a case where the distance D between the ultrasonic transducer 17B and the inspection region of the object to be inspected 19B is appropriately maintained. Specifically, FIG. 9(A) shows a case where the center of curvature of the arc of the arranged piezoelectric transducers 35 substantially accords with the center of curvature of the arc of the corner portion surface constituting the inspection region of the object to be inspected 19B. Thus, when the distance D between the ultrasonic transducer 17B and the inspection region of the object to be inspected 19B is appropriately maintained, as shown in FIG. 9(B), the distance D between the piezoelectric transducer 35 and the inspection region of the object to be inspected 19B becomes constant and the maximum difference X is 0.

FIG. 10(A) shows a case where the distance D between the ultrasonic transducer 17B and the inspection region of the object to be inspected 19B is short. When the distance D between the ultrasonic transducer 17B and the inspection region of the object to be inspected 19B is short, as shown in FIG. 10(B), the distance D between the piezoelectric transducer 35i located substantially at the center and the inspection region of the object to be inspected 19B is smaller than the appropriate distance, and the maximum difference X becomes minus.

FIG. 11(A) shows a case where the distance D between the ultrasonic transducer 17B and the inspection region of the object to be inspected 19B is long. When the distance D between the ultrasonic transducer 17B and the inspection region of the object to be inspected 19B is long, as shown in FIG. 11(B), the distance D between the piezoelectric transducer 35i located substantially at the center and the flaw inspection surface of the object to be inspected 19B is larger than the appropriate distance, and the maximum difference X becomes plus.

Further, though not shown, even in a case where the ultrasonic transducer 17B does not provide an appropriate tilt with respect to the inspection region of the object to be inspected 19, a plot showing the distance D between the piezoelectric transducer 35 and the inspection region of the object to be inspected 19B obtained from the appropriate reflection echo as in FIG. 9(B) cannot be obtained, thus detecting the tilt therefrom.

The distance and tilt calculation unit 60 calculates information on the distance and the tilt between the piezoelectric transducer 35 and the inspection region of the object to be inspected 19B thus detected from the reflection echo of the piezoelectric transducer 35 and outputs the information to an integral ultrasonic transducer control device 6B.

In the integral ultrasonic transducer control device 6B, a control amount calculation unit 22 calculates control amounts of a distance controlling actuator 15 and a tilt controlling actuator 16 based on the information on the distance and the tilt output from the flaw inspection device 7B.

The control amounts of the distance controlling actuator 15 and the tilt controlling actuator 16 calculated by the control amount calculation unit 22 are output as control signals to the distance controlling actuator 15 and the tilt controlling actuator 16, respectively. The controlling actuators 15 and 16 are driven in response to the control signals.

The ultrasonic flaw inspection using the ultrasonic inspection apparatus of this embodiment is substantially the same as the ultrasonic flaw inspection described in the second embodiment, and detailed descriptions thereof will be omitted herein.

With the ultrasonic inspection apparatus, in addition to the advantageous effect achieved by the ultrasonic inspection apparatus of the first and second embodiments, the ultrasonic transducer 17B is provided in the arcuate shape, and thus, a deviation from an ideal scanning position can be detected even if the inspection region of the object to be inspected 19B is a corner portion. Since the integral ultrasonic transducer 2B absorbs the deviation, the ultrasound can be reliably incident on the surface of the object to be inspected 19B at a constant angle, and a constant distance can be maintained between the center of the opening surface of the ultrasonic transducer 17 and the surface of the object to be inspected 19. Thus, the ultrasonic inspection apparatus of this embodiment allows ultrasonic flaw inspection to be performed with high accuracy.

In this embodiment, although the inside of the corner portion of the object to be inspected 19 is explained as the inspection region, an ultrasonic flaw inspection of the outside of the corner portion of the object to be inspected 19 may be performed.

Furthermore, although the distance between the piezoelectric transducer 35 and the flaw inspection surface of the object to be inspected 19 is calculated from the reflection echo of the piezoelectric transducer 35 in the ultrasonic transducer 17B, it may be calculated using flaw inspection image information generated by the signal processing unit 33 performing a series of imaging processes such as A/D conversion and visualization.

Fourth Embodiment

An ultrasonic inspection apparatus according to a fourth embodiment of the present invention will be described hereunder.

The ultrasonic inspection apparatus of the fourth embodiment is different from the ultrasonic inspection apparatus of the third embodiment in that a scanner mechanism includes a corner copying mechanism.

Figure 12:
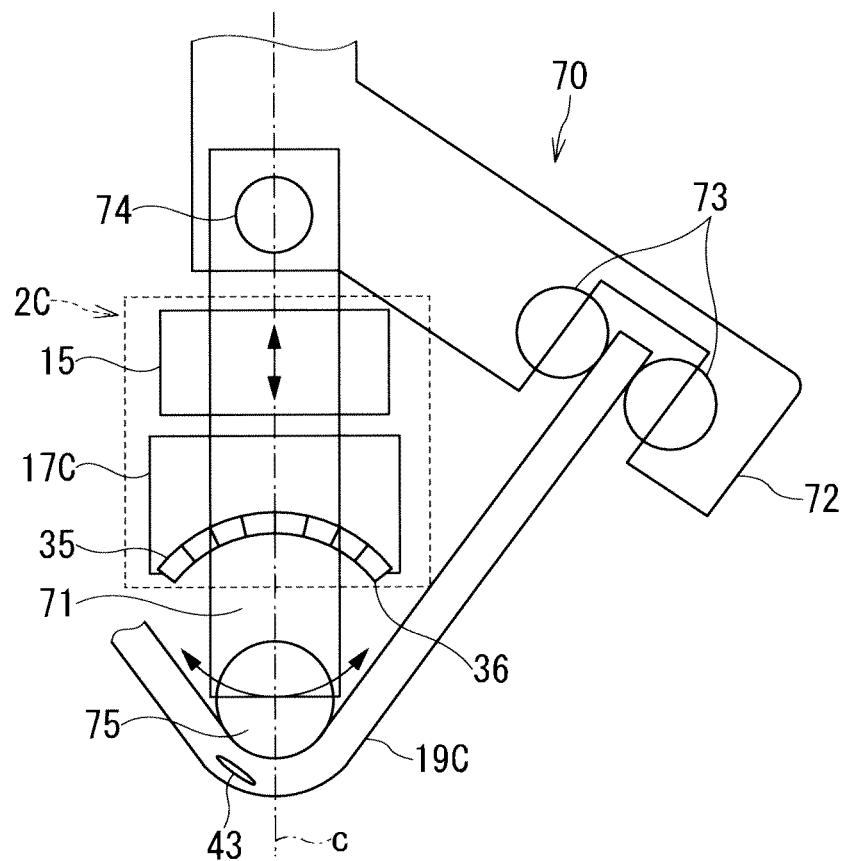
FIG. 12 is a schematic configuration diagram of a corner copying mechanism of an ultrasonic inspection apparatus according to a fourth embodiment of the present invention.

FIG. 12 is a schematic configuration diagram of a part of a corner copying mechanism 70 and an integral ultrasonic transducer 2C of the ultrasonic inspection apparatus according to the fourth embodiment of the present invention. Configurations and components corresponding to those in the first to third embodiments are denoted by the same reference numerals, and overlapping descriptions will be omitted herein.

In the ultrasonic inspection apparatus of this embodiment, a scanner mechanism 3 includes a corner copying mechanism 70.

The ultrasonic flaw inspection apparatus of the third embodiment detects a deviation between a scanning position based on scanning path information of an ultrasonic transducer 17C and an ideal scanning position, and the integral ultrasonic transducer 2C absorbs the deviation. The corner copying mechanism 70 provided in the ultrasonic flaw inspection apparatus of this embodiment is provided for maintaining the ultrasonic transducer 17C after a deviation correction process held in an ideal scanning position. Specifically, the corner copying mechanism 70 is provided to maintain the ultrasonic transducer 17C in a position where a center of curvature of an arc of arranged piezoelectric transducers 35 substantially accord with a center of curvature of an arc of a corner portion surface that is an inspection region of the object to be inspected 19C in an ultrasonic flaw inspection.

The corner copying mechanism 70 is composed of a corner copying portion 71, a fulcrum position adjustment portion 72, and a roller 73.

The fulcrum position adjustment portion 72 is provided in, for example, an unshown scanner mechanism 3. A pair of rollers 73 are provided at one end of the fulcrum position adjustment portion 72. The two rollers 73 are secured to sandwich front and back surfaces of a flat portion of the object to be inspected 19C. The rollers 73 vertically hold the flat portion of the object to be inspected 19C and a length directional portion of the fulcrum position adjustment portion 72. A fulcrum 74 is provided at the other end of the fulcrum position adjustment portion 72. The fulcrum position adjustment portion 72 appropriately adjusts and holds the object to be inspected 19C to adjust the fulcrum 74 to be located on a central axis C passing the center of curvature of the corner portion of the object to be inspected 19C.

The corner copying portion 71 that rotates around the fulcrum 74 is connected to the fulcrum position adjustment portion 72. The corner copying portion 71 holds an integral ultrasonic transducer 2C including a distance controlling actuator 15, an ultrasonic transducer 17C and the like around the fulcrum 74. A roller 75 is provided at a lower end of the corner copying portion 71 so as to rotate around an axis perpendicular to a longitudinal direction of the corner copying portion 71 (axis extending in a direction perpendicular to the drawing paper). The roller 75 is rotatable in contact with a surface (corner portion) of the object to be inspected 19C. The integral ultrasonic transducer 2C and the roller 75 are located on the central axis C in accordance with the adjustment of a position of the fulcrum 74 by the fulcrum position adjustment portion 72 via the corner copying portion 71.

Although FIG. 12 shows a part of the configuration of the integral ultrasonic transducer 2C, the integral ultrasonic transducer 2C may include the tilt controlling actuator 16 and the integral ultrasonic transducer control device 6, which are not shown in FIG. 12.

The corner copying mechanism 70 thus configured brings the roller 75 into contact with the corner portion that is the inspection region of the object to be inspected 19C to maintain the integral ultrasonic transducer 2C in an appropriate position. Thus, the ultrasound emitted from each of the piezoelectric transducers 35 in the ultrasonic transducer 17C can intersect the corner portion that is the inspection region of the object to be inspected 19C and have substantially the same emission distance between each piezoelectric transducer 35 and the corner portion surface.

With the ultrasonic inspection apparatus 1, for the integral ultrasonic transducer 2C after the deviation correction process, a scanning position of the ultrasonic transducer 17C with respect to the object to be inspected 19C can be maintained in an appropriate position where the ultrasound intersects the corner portion surface and has substantially the same distance between each piezoelectric transducer 35 and the corner portion surface.

In this embodiment, although the inside of the corner portion of the object to be inspected 19C is explained as the inspection region, the ultrasonic flaw inspection may be performed to the outside of the corner portion of the object to be inspected 19C.

The invention claimed is:

1. An ultrasonic inspection apparatus comprising:
    an ultrasonic transducer, in which a plurality of piezoelectric transducers are arranged, emits ultrasound to an inspection region of an object to be inspected and receives a reflection echo of the ultrasound;
    a flaw inspection device that causes the ultrasonic transducer to emit the ultrasound, detects and calculates an electric echo signal of the reflection echo received by the ultrasonic transducer, and generates flaw inspection image information of the inspection region of the object to be inspected;
    a scanner mechanism that drives the ultrasonic transducer on the object to be inspected based on previously generated scanning path information;
    a distance and tilt calculation unit that calculates, a distance and a tilt between an opening surface of the ultrasonic transducer and the inspection region of the object to be inspected, simultaneously with the movement of the ultrasonic transducer driven by the scanner mechanism;
    a control unit that calculates, based on the distance and the tilt calculated by the distance and tilt calculation unit, a deviation between a scanning position based on the scanning path information and a predetermined scanning position where a normal line to the inspection region of the object to be inspected and the opening surface of the ultrasonic transducer intersect each other and where the ultrasonic transducer and the inspection region of the object to be inspected are located with a predetermined distance therebetween, and generates a control signal for correcting the distance and the tilt between the opening surface of the ultrasonic transducer and the inspection region of the object to be inspected to the predetermined scanning position in accordance with the thus calculated deviation; and
    a driving mechanism that operates independently from the scanner mechanism and drives the ultrasonic transducer to the predetermined scanning position in response to the control signal generated by the control unit,
    wherein at least the ultrasonic transducer and the driving mechanism are integrally formed as an integral ultrasonic transducer.

2. The ultrasonic inspection apparatus according to claim 1, wherein the ultrasonic transducer further includes a set of multiple distance measuring sensors that are provided with a known space therebetween and output distance information between the ultrasonic transducer and the inspection region of the object to be inspected by optical measurement or ultrasound measurement, and the distance and tilt calculation unit calculates the distance and the tilt between a center of the opening surface of the ultrasonic transducer and the inspection region of the object to be inspected based on the distance information output from the distance measuring sensors.

3. The ultrasonic inspection apparatus according to claim 1, wherein the distance and tilt calculation unit calculates the distance and the tilt between the opening surface of the ultrasonic transducer and the inspection region of the object to be inspected in response to at least one of the electric echo signal of the reflection echo detected by the flaw inspection device and the flaw inspection image information of the inspection region of the object to be inspected generated by the flaw inspection device.

4. The ultrasonic inspection apparatus according to claim 3, wherein the control unit sets, as the predetermined scanning position, a position where a center of curvature of the ultrasonic transducer including the piezoelectric transducers arranged in an arcuate shape accords with a center of curvature of a corner portion as the inspection region of the object to be inspected, and calculates a deviation between the scanning position based on the scanning path information and the predetermined scanning position.

5. The ultrasonic inspection apparatus according to claim 4, further comprising:
    a roller that rotates in contact with the corner portion;
    a corner copying portion that holds the roller and the ultrasonic transducer around a fulcrum; and
    a fulcrum position adjustment portion that is connected to the corner copying portion via the fulcrum, adjusts and holds the object to be inspected so that the fulcrum is held on a central axis passing the center of curvature of the corner portion to thereby place the roller and the ultrasonic transducer held by the connected corner copying portion on the central axis.

6. The ultrasonic inspection apparatus according to claim 1, further comprising:
    a shoe member including a soft shoe insertion portion provided on a contact surface of the object to be inspected and tightly secured to the contact surface of the object to be inspected via a liquid couplant; and
    a soft shoe that is more flexible than the shoe member, has substantially the same shape as the soft shoe insertion portion, and is detachably fitted into the soft shoe insertion portion via the liquid couplant,
    wherein the shoe member and the soft shoe have thicknesses determined in accordance with a sound speed ratio between the shoe member and the soft shoe.

* * * * *